United States Patent [19]
Chiozza

[11] Patent Number: 4,553,536
[45] Date of Patent: Nov. 19, 1985

[54] INTRAUTERINE CONTRACEPTIVE DEVICE

[75] Inventor: Enrico Chiozza, Rome, Italy

[73] Assignee: Uniderm Farmaceutici s.n.c., Rome, Italy

[21] Appl. No.: 469,448

[22] Filed: Feb. 24, 1983

[51] Int. Cl.⁴ .............................................. A61F 5/46
[52] U.S. Cl. .................................................... 128/130
[58] Field of Search ................................ 128/127–131

[56] References Cited
U.S. PATENT DOCUMENTS

| | | | |
|---|---|---|---|
| Re. 30,312 | 6/1980 | Kessel | 128/130 |
| 3,789,838 | 2/1974 | Fournier et al. | 128/130 |
| 3,881,475 | 5/1975 | Gordon et al. | 128/130 |

Primary Examiner—C. Fred Rosenbaum
Attorney, Agent, or Firm—Cushman, Darby & Cushman

[57] ABSTRACT

An intrauterine contraceptive device comprising two curved arms, lying on offset planes, having one end integral to a sleeve and the other end free, and a post, engaged in a not removable way with the sleeve, made of plastic material incorporating micronized copper powder. The particular configuration of the device hinders the ejection of the device due to womb shrinking forces (FIG. 1).

7 Claims, 2 Drawing Figures

INTRAUTERINE CONTRACEPTIVE DEVICE

The present invention relates to a device, usually called "spiral" or "IUD", which can be introduced into a woman's womb to prevent fecundation.

At present, various devices of the above mentioned kind are well known, which, however, have some drawbacks in practical use.

In fact, they may tend to be ejected owing to womb contractions, may not be absolutely safe as contraceptives, are difficult to be inserted and extracted and have a comparatively short effective life.

It is an object of the present invention to produce an intrauterine contraceptive device, the configuration of which makes it possible to avoid or, at least, to reduce the abovementioned drawbacks.

SUMMARY OF THE INVENTION

An object of the present invention is an intrauterine contraceptive device, comprising two arms, each arm having one fixed end and the other end free, and a post supporting the fixed ends of said arms. Each one of said arms extends on one side of the post from said fixed end and then is curved along more than a half circle that the free end thereof projects beyond said post, said post being always interposed between said two arms so that said arms always lie on respective offset planes.

Another object of the present invention is the use of a plastic material for forming the device, in which a micronised copper powder is incorporated.

As it is well known, metal ions, particularly copper ions, increase the prolification of leukocytes, which prevents fertilisation. Furthermore the incorporation of copper gives the device a pleasant copper color.

DETAILED DESCRIPTION OF THE INVENTION

One example of the present invention, in a preferred embodiment thereof, is illustrated in the accompanying drawing, wherein.

Figure 1:
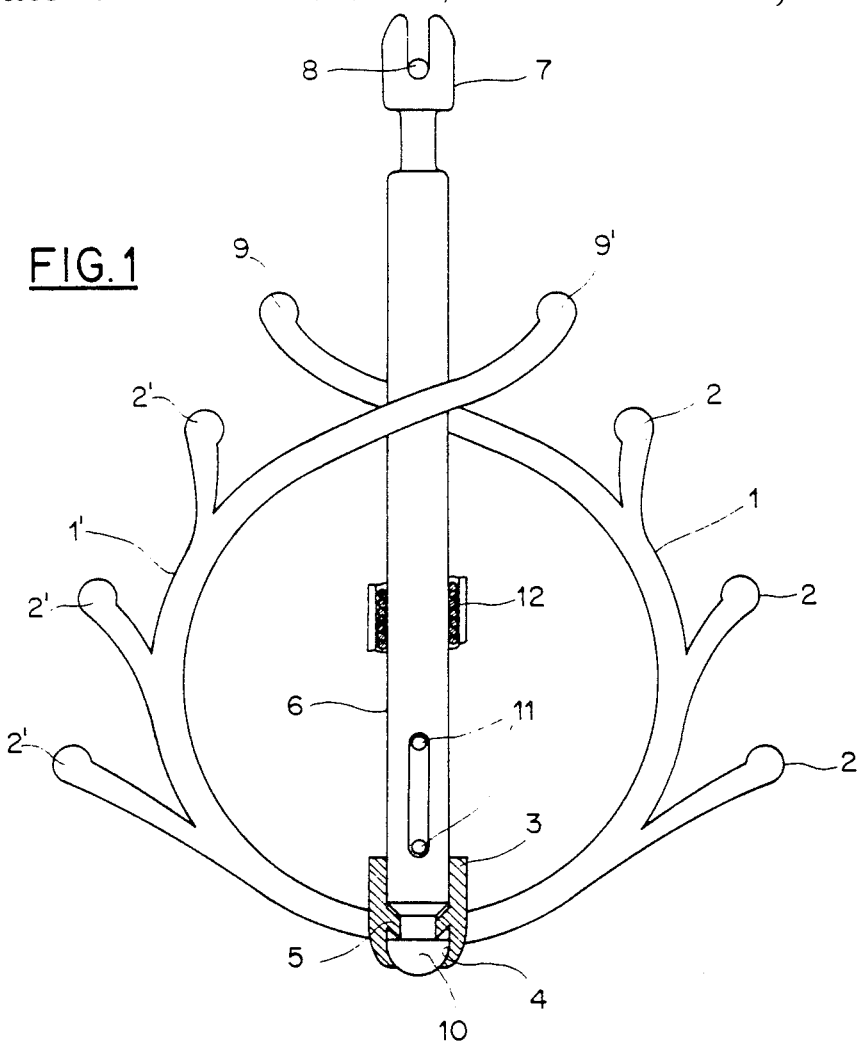
FIG. 1 is a plan view of the present device.

Referring to the drawing, 1 and 1' indicate two arms of the spiral respectively, essentially similar one to the other. Each arm 1, 1' is a curved thin resilient element. Said arms 1, 1' have a free end 9, 9', said end being rounded off. Said arms 1, 1' show moreover branches 2 and 2', three in the present embodiment, with the ends rounded off for enhancing adherence of the device to the womb wall. The other end of each arm 1, 1' is integral to a sleeve 3. Blocking tongues 5 project into a hole 4 of said sleeve 3, which tongues 5 aid in blocking the head 10 of a post 6 in a not removable way. Said post 6 is made of a cylindrical rod extending for a certain length beyond the free ends 9, 9' of the arms 1, 1' in a central position with respect to said arms 1, 1'. In the free end 7 of said post 6 a through transversal hole 8 is formed. Said hole 8 is of use for securing a thread, usually a nylon thread, for the extraction, when necessary or desired, of the spiral from the womb. In said post 6, near said sleeve 3, two holes 11 are formed to secure, similarly to already known devices, a winding (indicated in 12) of a copper wire placed on the outer surface of said post 6. On said post 6 it is also possible to form grooves (not shown) for having further metallic elements and enlarging the surface of said copper wire winding 12.

The distinctive feature of the device of the present invention is the configuration and arrangement of the arms 1, 1' which make said device remarkably improved in comparison with conventional devices.

Figure 2:
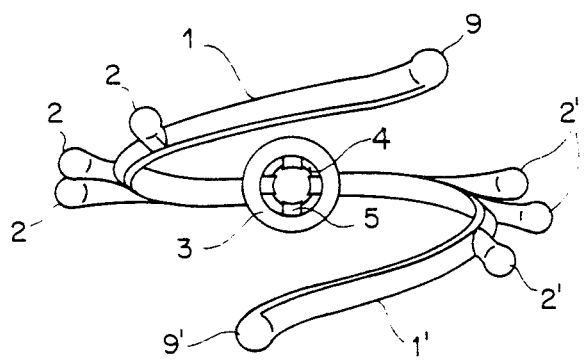
FIG. 2 is a front view from one end of the device, with the post removed.

Particularly the arms 1, 1' lie on different offset planes (see FIG. 2) and the free ends 9, 9' thereof cross one another, the post 6 being always interposed between them, so that each of said free ends 9, 9' remains on the side of said post 6 opposite to the side where the fixed end of the respective arm 1, 1' lies.

The previously described arrangement provides an extraordinary firm fixing inside the womb of the device according to the present invention, said fixing preventing any possibility of an unintentional ejection. In fact, as the womb shrinking forces are responsible for a possible ejection, by acting on said ends 9, 9' between which said post 6 is placed, the very same forces will, by reaction, cause the arms 1, 1' to be stretched apart. As a consequence, the securing branches 2 will adhere more firmly to the womb walls. If, on the contrary, said womb shrinking forces act, through said fixing branches 2, 2' on said arms 1, 1', they will cause the arms 1, 1' to get closer and said free ends 9, 9' to set apart. As a consequence said free ends 9 and 9' will adhere more firmly to the womb walls, so still ensuring against ejection.

The materials used for making the present device can be the same or different for each component. Preferably plastic materials are used, incorporating metallic powder which are produced, for example, by an intimate mixing of a very fine plastic powder with a very fine copper powder, said mixture being then molded to obtain the elements of the device of the invention.

Preferably said post only is made of said copper incorporating material.

The intrauterine contraceptive device according to the present invention, has an effective life of more than 3 years and provides a sure contraceptive effectiveness, without drawbacks, frequent in similar devices, such as spotting, abdomen pain and the like.

Such drawbacks, related to the rigidy of usual plastic materials, do not take place in the case of the device according to the present invention, owing to the particularly resilient and soft configuration thereof.

Although the present invention has been described in a considerable detail, many variations may be made within the scope of the following claims, without departing from the spirit thereof.

What is claimed is:

1. An intrauterine contraceptive device comprising a rigid post having an insertion end and a sleeve pivotally connected at the insertion end, said sleeve being freely rotatable around the axis of the post, a pair of arms being integral with said sleeve, each arm being positioned opposite from the other and extending outwardly from the longitudinal axis of the sleeve, each arm having an essentially circular curve having the concave portion facing towards the post, the free end of said arms extending for a minor length beyond the post with respect to the rest of the arm such that the post is interposed between and extends beyond the pair of arms thereby preventing the arms from contacting each other the arms lying in a plane essentially parallel to and spaced from the axis of the post.

2. The intrauterine device according to claim 1 where the device includes a spermacidally active component.

3. The intrauterine device according to claim 2 where the spermacidally active component comprises a copper wire wound around at least a portion of the post.

4. The intrauterine device according to claim 1 wherein the device is formed of a plastic material containing an ionizable metal powder as a spermacidally active component.

5. The intrauterine device according to claim 4 wherein the plastic material includes micronized copper powder.

6. The intrauterine device according to claim 1 where at least one thread is secured to the post for extraction of the device.

7. An intrauterine contraceptive device comprising a rigid post having an insertion end and a sleeve pivotally connected at the insertion end and freely rotatable around the axis of the post, a pair of arms for contacting the uterus integral with the sleeve, each arm being positioned opposite one another and extending outwardly from the longitudinal axis of the sleeve, each arm having an essentially circular curve having a concave and a convex face, the concave face directed toward the post, the free ends of said arms extending for a minor length beyond the post with respect to the rest of the arm such that a uterine contraction on the convex face of the arm causes an outward movement of the free ends to engage the uterus opposing an expulsion action of the uterus, the post being interposed between and extending beyond the pair of arms.

* * * * *